(12) United States Patent
Bond-Thorley et al.

(10) Patent No.: US 9,347,918 B2
(45) Date of Patent: May 24, 2016

(54) ULTRASONIC ARRAY FOCUSSING APPARATUS AND METHOD

(75) Inventors: Andrew Bond-Thorley, Stonehouse (GB); Richard Freemantle, Asbourne (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 59 days.

(21) Appl. No.: 13/990,657

(22) PCT Filed: Nov. 24, 2011

(86) PCT No.: PCT/GB2011/052307
§ 371 (c)(1),
(2), (4) Date: May 30, 2013

(87) PCT Pub. No.: WO2012/073002
PCT Pub. Date: Jun. 7, 2012

(65) Prior Publication Data
US 2013/0239689 A1    Sep. 19, 2013

(30) Foreign Application Priority Data
Nov. 30, 2010    (GB) .................................. 1020249.7

(51) Int. Cl.
*G01N 29/24* (2006.01)
*G01N 29/22* (2006.01)
*G01N 29/26* (2006.01)

(52) U.S. Cl.
CPC .......... *G01N 29/2456* (2013.01); *G01N 29/221* (2013.01); *G01N 29/2487* (2013.01); *G01N 29/262* (2013.01); *G01N 2291/263* (2013.01); *G01N 2291/2694* (2013.01)

(58) Field of Classification Search
CPC ... G01N 29/04; G01N 29/24; G01N 29/2456; G01N 29/221; G01N 29/262; G01N 29/2487; G01N 2291/263; G01N 2291/2694
USPC ............................ 73/625, 638, 622, 623, 640
See application file for complete search history.

(56) References Cited

U.S. PATENT DOCUMENTS

| | | |
|---|---|---|
| 3,699,805 A | 10/1972 | Bayre |
| 4,297,886 A | 11/1981 | Anikeev et al. |
| 4,319,490 A | 3/1982 | Hartmann, Jr. |
| 4,516,583 A | 5/1985 | Richard |
| 4,794,929 A * | 1/1989 | Maerfeld ............... G10K 11/30 600/443 |
| 5,235,986 A | 8/1993 | Maslak et al. |

(Continued)

FOREIGN PATENT DOCUMENTS

| | | |
|---|---|---|
| EP | 1241994 A2 | 9/2002 |
| EP | 1764614 A1 | 3/2007 |

(Continued)

OTHER PUBLICATIONS

International Search Report and Written Opinion for PCT/GB2011/052307, Jun. 3, 2012.

(Continued)

*Primary Examiner* — Laura Martin
*Assistant Examiner* — Suman K Nath
(74) *Attorney, Agent, or Firm* — Hauptman Ham, LLP

(57) ABSTRACT

A method is provided in which radiussed components are scanned by moving the focal point of a curved array into the component, while keeping the geometric focal point of the array coincident with that of the radiussed component.

15 Claims, 8 Drawing Sheets

(56) References Cited

U.S. PATENT DOCUMENTS

| | | | |
|---|---|---|---|
| 6,719,449 B1 * | 4/2004 | Laugharn, Jr. | B01F 11/02 366/127 |
| 7,454,973 B2 * | 11/2008 | Baba | G01N 29/043 600/443 |
| 7,644,618 B2 * | 1/2010 | Fetzer | G01N 29/225 73/632 |
| 7,836,768 B2 * | 11/2010 | Young | G01N 29/041 73/620 |
| 2001/0031922 A1 | 10/2001 | Weng et al. | |
| 2005/0075572 A1 | 4/2005 | Mills et al. | |
| 2005/0096542 A1 | 5/2005 | Weng et al. | |
| 2005/0240127 A1 | 10/2005 | Seip et al. | |
| 2007/0068253 A1 | 3/2007 | Carodiskey | |
| 2008/0314154 A1 * | 12/2008 | Fetzer | G01N 29/2468 73/638 |
| 2009/0211631 A1 * | 8/2009 | Temchenko et al. | 136/256 |
| 2010/0124142 A1 * | 5/2010 | Laugharn, Jr. | G10K 15/00 366/108 |

FOREIGN PATENT DOCUMENTS

| | | |
|---|---|---|
| FR | 2736790 A1 | 1/1997 |
| GB | 1222355 A | 2/1971 |
| GB | 2033579 A | 5/1980 |
| JP | 2001-327489 A | 11/2001 |
| JP | 2004-340809 A | 12/2004 |
| JP | 2008-228873 A | 10/2008 |
| WO | 0145550 A3 | 6/2001 |

OTHER PUBLICATIONS

British Search Report for GB1020249.7, dated Feb. 28, 2011.
British Search Report for GB1020249.7, dated Apr. 14, 2011.

* cited by examiner

ULTRASONIC ARRAY FOCUSSING APPARATUS AND METHOD

RELATED APPLICATIONS

The present application is a National Phase of International Application Number PCT/GB2011/052307, filed Nov. 24, 2011, and claims priority from British Application Number 1020249.7, filed Nov. 30, 2010.

The present invention relates to an ultrasonic array focussing apparatus and method. More particularly, the present invention relates to a phased array focussing apparatus and method used in the engineering, and in particular aircraft, industry to inspect parts having small radius features such as stringers.

Known ultrasonic arrays in the aircraft inspection field have the ability to detect discontinuities of around 6×6 mm. With the increasing use of composite materials in aircraft design, the ability to detect discontinuities within the laminate structure of, for example, carbon fibre reinforced polymers has become increasingly important.

Discontinuities such as fibre waviness and porosity in the material may detrimentally affect the mechanical properties of the structure. These discontinuities can be small (having dimensions less than the 6×6 mm standard discussed above). Such discontinuities therefore have to be "designed in" to the structure—meaning the components have to be larger to account for any inherent weakness in the material. This is undesirable as it leads to increased cost and weight of the aircraft assembly.

Ultrasonic testing utilises a probe having one or more ultrasonic elements which emit ultrasonic pulses into the material being inspected. The pulses are reflected by features within the material's structure (such as discontinuities) and return to the surface of the material where they can be detected. The time taken for the pulse to return to the probe is indicative of the location of the defect in the material (as the speed of sound in the material is generally predictable).

Such probes may comprise a series of elements in an array. For example a linear array comprises a straight, linear row of elements known as a one dimensional, "1-D" array. If fired simultaneously, the elements create a generally linear, constructive wavefront which propagates in a direction parallel to, and away from, the array.

Such arrays can be focussed by altering the element firing times. A phased array is controlled such that the elements are fired at different times, i.e. each element has a specific delay following the firing of the first element. A result of this is that the constructive wavefront produced by the array can be focussed in specific areas of the material being inspected. The scheme determining by how much each element of the array is delayed is known as a "focal law".

A problem with known 1-D phased arrays is that the phasing effect only provides focus in the plane of the array (i.e. "cylindrical" focus). The resolution of the array in a direction perpendicular thereto is not improved by phasing. This problem can be mitigated by shaping the array to produce an "elevation focus". Different elevation focussing requirements will require several different separate arrays, or the use of an expensive two dimensional "2-D" array and control system.

Unphased curved arrays have a focus resulting from their geometry. For example, if an array comprises a plurality of elements describing a circle segment, and each element of the array is fired simultaneously, the array has a focal point at the circle origin.

It is known to use curved probes to inspect radiused components. Generally, the focal point is aligned with the origin of the component radius so that the ultrasonic pulses enter the radiused component normal to the surface. This is satisfactory for large discontinuities (typically 6×6 mm).

Most radiused components in the aerospace sector have a thickness less than the radius of curvature. A problem with using curved arrays on components of this type is that the focal point of the array is not within the material (it will typically lie between the probe and the component, or on the other side of the component to the probe, at the centre of curvature of the array). Therefore smaller discontinuities are not detected because the array is configured for breadth of coverage as opposed to resolution.

It is an aim of the invention to overcome, or at least mitigate, the above problems.

According to a first aspect of the invention there is provided a method of scanning a curved engineering component comprising the steps of:

providing a probe having a curved ultrasonic array having a plurality of elements arranged in a curved path having a geometric focal point, providing a control system configured to fire the elements of the array according to a predetermined focal law, providing a curved engineering component having a radius and centre of curvature, which centre of curvature is outside the component, aligning the geometric focal point of the array and the centre of curvature of the curved engineering component, using the control system to activate the elements of the array according to a focal law to move the focal point of the array away from the geometric focal point into the workpiece.

The present invention therefore allows the ultraonic energy from the array to be focussed within the workpiece to allow a high resolution image to be produced, and small defects to be detected. The invention also provides the benefit of allowing the ultrasonic energy to pass into the workpiece in a direction normal to the workpiece surface, which is beneficial for scanning and reduces distortion.

Preferably the curved path of the curved ultrasonic array defines a first plane, and the method comprises the step of:

providing a focussing element for the curved ultrasonic array comprising a curved surface arranged to focus ultrasonic energy from the array, positioning the scanning element proximate the array to focus ultrasonic energy from the array in a second plane, perpendicular to the first plane.

This allows the higher resolution electronic focussing approach adopted in the first plane to be complemented in the second plane by mechanical or lens focussing.

Preferably the focussing element comprises:

a first, input, surface proximate the array, the first surface being flat in the second plane, and;

a second, output, surface being curved in the second plane to focus ultrasonic energy leaving the focussing element.

Preferably the curved path is a circle segment having a geometric focal point at the origin of the circle segment.

Preferably the workpiece comprises a radiused portion.

The ultrasonic array may be flexible.

According to a second aspect of the invention there is provided an engineering component inspection ultrasonic probe for inspection of radiused components comprising;

a probe having a curved ultrasonic array having a plurality of elements arranged in a curved path having a geometric focal point, a control system configured to fire the elements of the array according to a predetermined focal law, which the control system is configured to activate the elements of the array according to a focal law to move the focal point of the array away from the geometric focal point into a workpiece.

Preferably the curved path lies in a first plane, and in which the probe comprises:

a focussing element comprising a curved surface arranged to focus ultrasonic energy from the array in a second plane, perpendicular to the first plane.

Preferably the curved surface is concave.

Preferably the curved surface describes a concave circle segment in cross section.

Preferably the focussing element comprises an input surface proximate the array, which input surface is flat in the second plane.

Preferably the focussing element comprises an input surface proximate the array, which input surface is curved in the first plane.

Preferably the focussing element is replaceable.

The above probe and method are applicable to the inspection of engineering components, and in particular composite engineering components in general. That said, the probe, focussing element and method are particularly suited to the inspection of aircraft components, and in particular composite aircraft components.

An example of an ultrasonic array focusing apparatus and method in accordance with the present invention will now be described with reference to the accompanying drawings in which.

Figure 1:
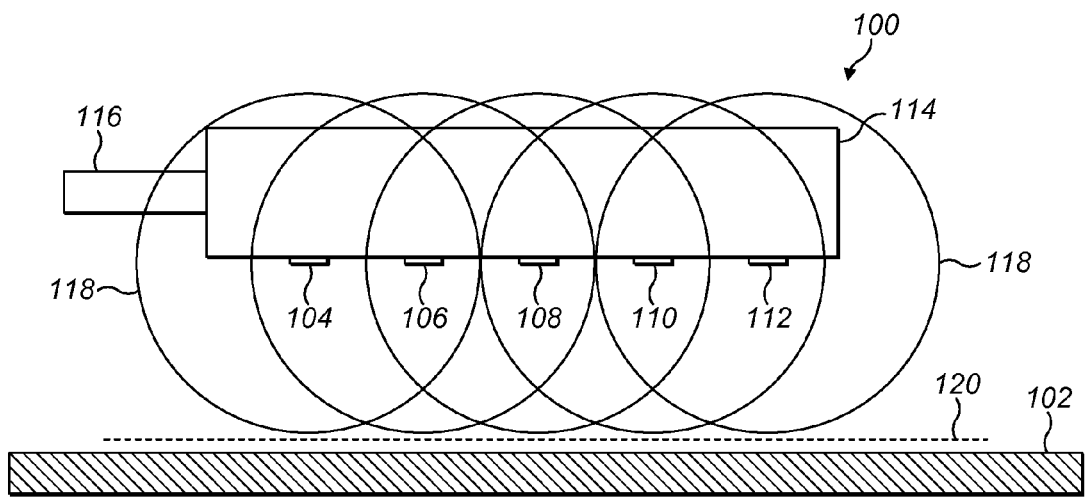
FIG. 1 is a schematic plan view of a flat linear 1-D array.

Referring to FIG. 1, a 1-D linear array 100 is shown proximate a workpiece 102. The linear array 100 comprises a first, second, third, fourth and fifth ultrasonic element 104, 106, 108, 110, 112, respectively which are mounted in an array housing 114 containing control hardware linked to an ultrasound system comprising a computer via a data connection 116 which carries the ultrasound signal. It will be noted that in practice, arrays having in the order of 128 elements are common, which in reality would be placed closer together than in the schematic view of these figures. In use, each of the elements can be fired simultaneously to produce a series of propagating ultrasonic pulses 118. It will be noted that in practice, groups of elements (e.g. 32 elements of a 128 element array) may be fired simultaneously to provide the desired effect.

Constructive interference of the ultrasonic pulses 118 forms a generally linear wave front 120 which enters the workpiece 102 and reflects back any discontinuities located in the material. The reflected pulses are also detected by the elements.

The linear array 100 as shown in FIG. 1 is an example of an unfocused array.

Figure 2:
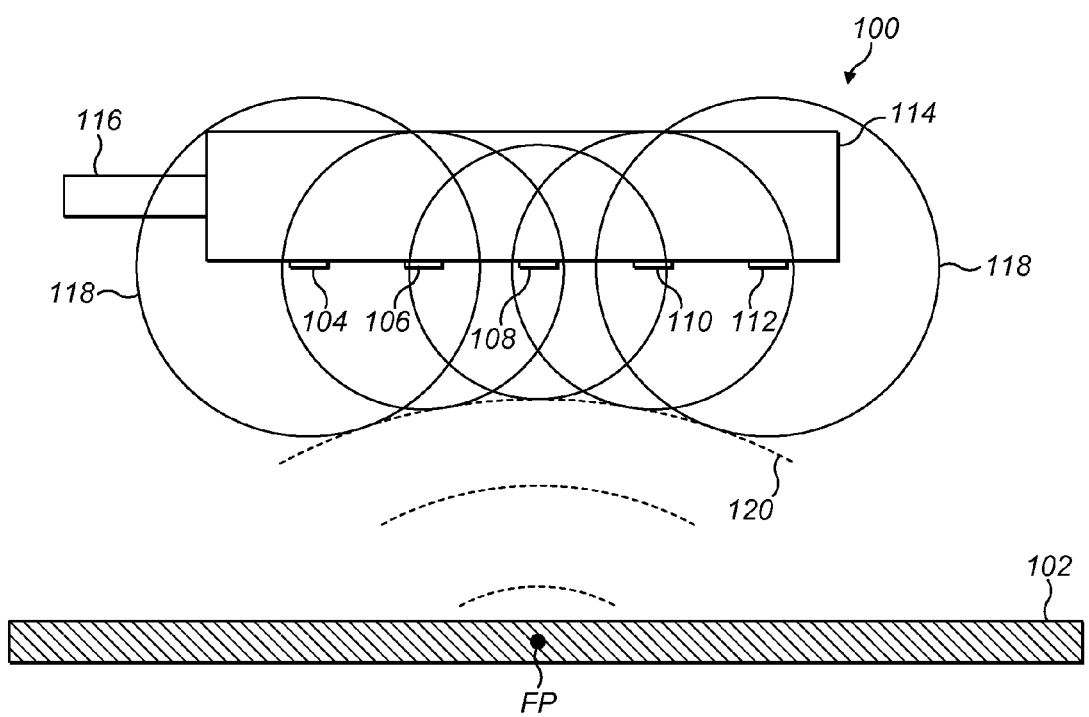
FIG. 2 is a view similar to that of FIG. 1 but with a focal law applied to the array.

Referring to FIG. 2, the same linear array 100 is shown except that a focal law has been applied to the elements 104, 106, 108, 110, 112. As such, the first and fifth elements 104, 112 fired first followed by the second and fourth elements 106, 110 and finally the third element 108. As such, the ultrasonic pulses 118 form a generally curved wave front 120 which converges towards a focal point FP within the workpiece 102.

The device of FIG. 2 is a phased array and the location of the focal point FP relative to the array can be adjusted by changing the focal law applied to the elements.

In the cases of both FIG. 1 and FIG. 2, the linear array 100 and the workpiece 102 are immersed in a couplant such as water. This enhances the transmission of the ultrasonic pulses 118 towards the workpiece 102 with minimal distortion.

It will also be noted that the focusing occurs in a first plane in which the elements are located, i.e. the plane of the page as shown in FIGS. 1 and 2. No focusing occurs in a second plane perpendicular to the plane of the page.

Figure 3:
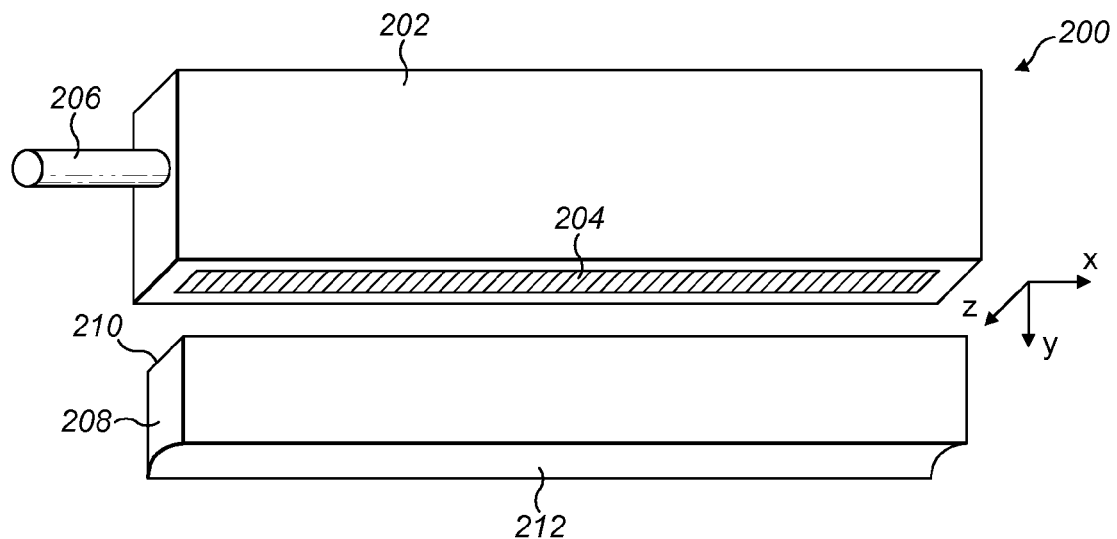
FIG. 3 is an exploded perspective view of a flat linear array assembly comprising a focusing element.

Referring to FIG. 3, a 1-D linear array 200 is shown comprising a housing 202 having a series of elements 204 arranged in a linear fashion in a direction X. The array 200 is connected to an ultrasound system comprising a suitable computer by data connection 206 which carries the ultrasound signal.

Each of the elements 204 faces in a direction Y perpendicular to X. As such, phasing of the array 200 can focus the array in the XY plane (the first plance). A focusing shoe 208 is provided having a substantially planar top surface 210 and a concave curved bottom surface 212 opposite the top surface 210.

Figure 4:
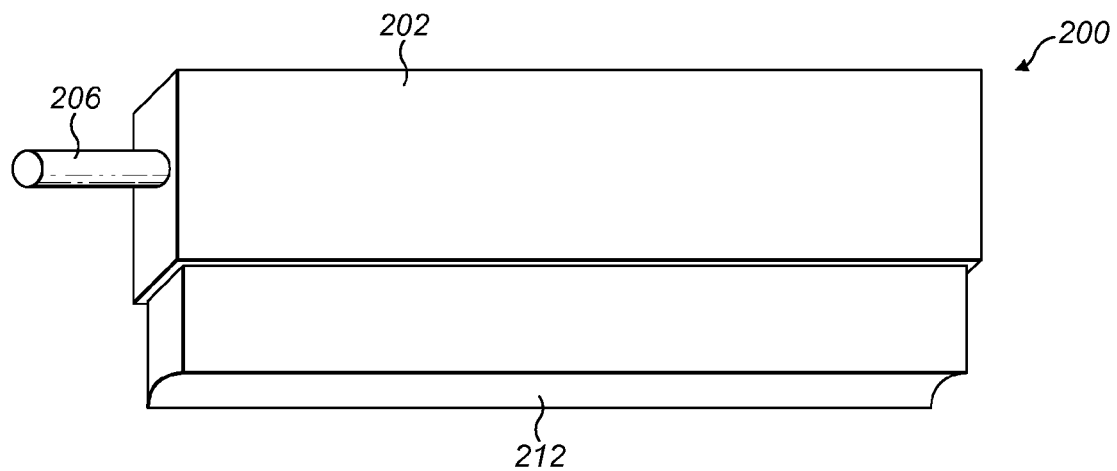
FIG. 4 is a perspective view of the array of FIG. 3 in an assembled condition.

Referring to FIG. 4, the focusing shoe 208 is assembled with the linear array 200 such that the planar top surface 210 is proximate the elements 204. As such, ultrasonic energy passes from the elements 204 into the focusing shoe 208. The ultrasonic energy leaves the focusing shoe 208 at the curved bottom surface 212. The focusing shoe 208 is constructed from a low ultrasonic attenuation material which permits the passage of ultrasonic energy with minimal distortion. In order to achieve this, the material has an acoustic impedance which is similar to that of water. As the ultrasonic energy leaves the focusing shoe 208, it is focused by the curved bottom surface 212 in the second, YZ, plane which is perpendicular to the first, XT plane. As such, the addition of the shoe provides better focusing for small discontinuities.

Figure 5:
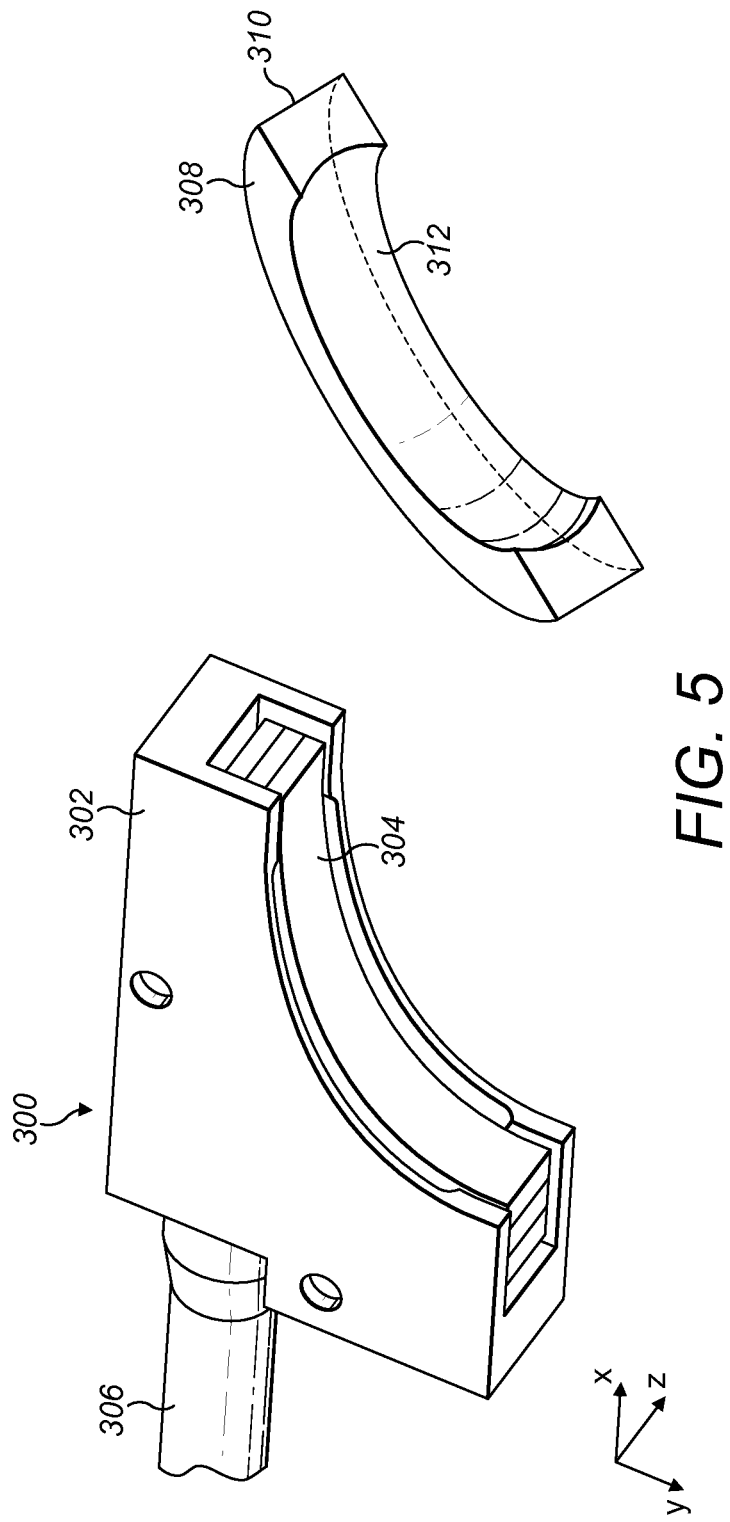
FIG. 5 is an exploded perspective view of a curved array comprising a focusing shoe according to the invention.

Referring to FIG. 5, a curved array 300 is shown having a housing 302, an array of elements 304 curved in a first XY plane and a data connection 306 which carries the ultrasonic signal. A curved focusing shoe 308 is provided having a top surface 310 which is curved in the XY plane (to match the surface 310 of the shoe 308) but substantially flat in the direction Z In other words, the top surface is flat in a series of second planes, all of which are parallel to axis Z but perpendicular to the XY plane. As such, the curved top surface 310 is suited to mate with the array of elements 304.

A concave curved bottom surface 312 is provided which is concave curved in the second planes parallel to Z, perpendicular to the first plance in XY. As such, out of XY plane focusing is provided for the curved array 300.

The above solution is particularly useful on very small radius components in which the discontinuities are particularly difficult to measure using traditional probes. The resolution of the probe can be considerably increased by using a focusing shoe of the above described type. It will also be noted that the shoe can be provided integrally with the probe if required.

Figure 6:
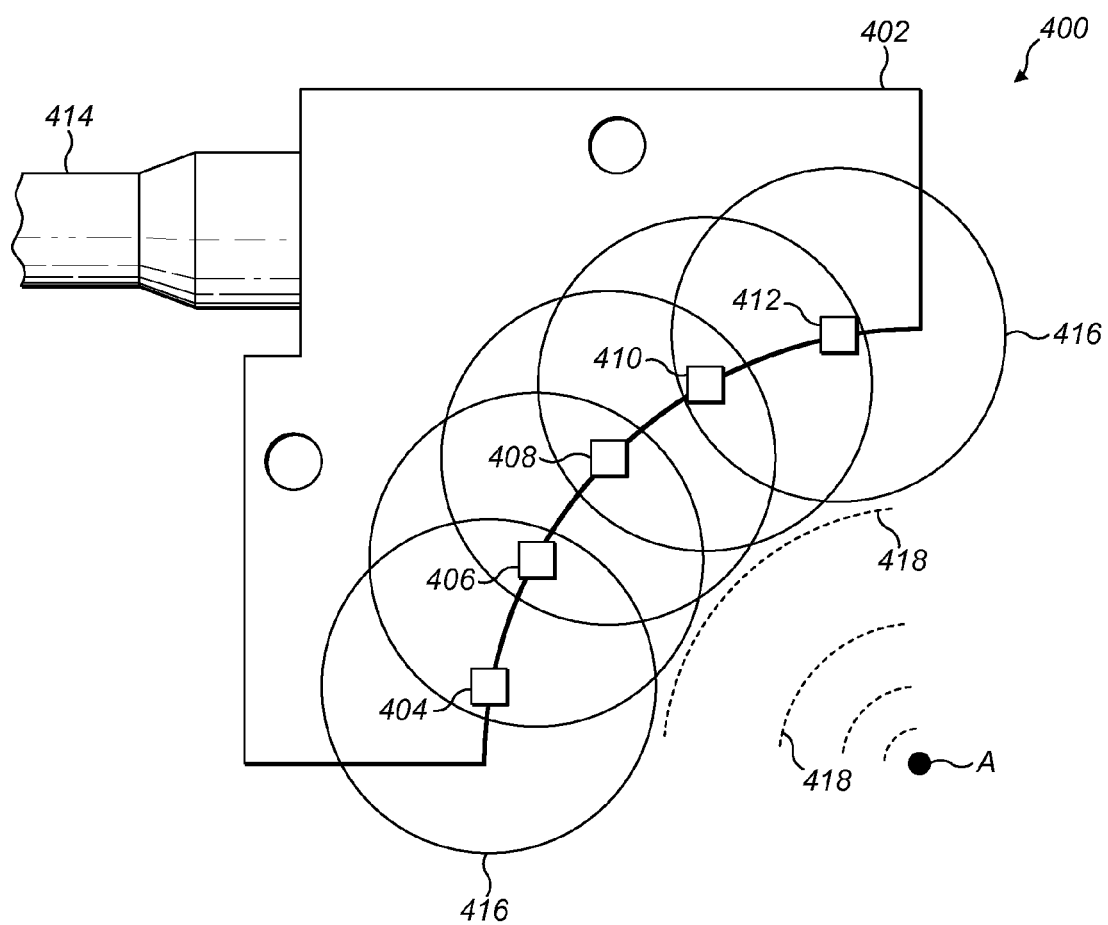
FIG. 6 is a schematic side view of a curved array.

Turning to FIG. 6, a curved array probe 400 is shown comprising a housing 402. The housing 402 houses a first, second, third, fourth and fifth element 402, 406, 408, 410, 412 respectively. It will be noted that in practice, arrays having in the order of 128 elements are common, which in reality would be placed closer together than in the schematic view of these figures. The elements are mounted about a 90 degree segment of a circle having an origin A. The elements are connected to control circuitry within the housing 402 which in turn is connected to a suitable computer via a datalink 414.

If fired simultaneously, each of the elements produces an ultrasonic pulse 416 which creates a circle segment wave front 418 due to constructive interference. The wave front 418 will propagate to a geometric focal point coincident with point A.

Figure 7:
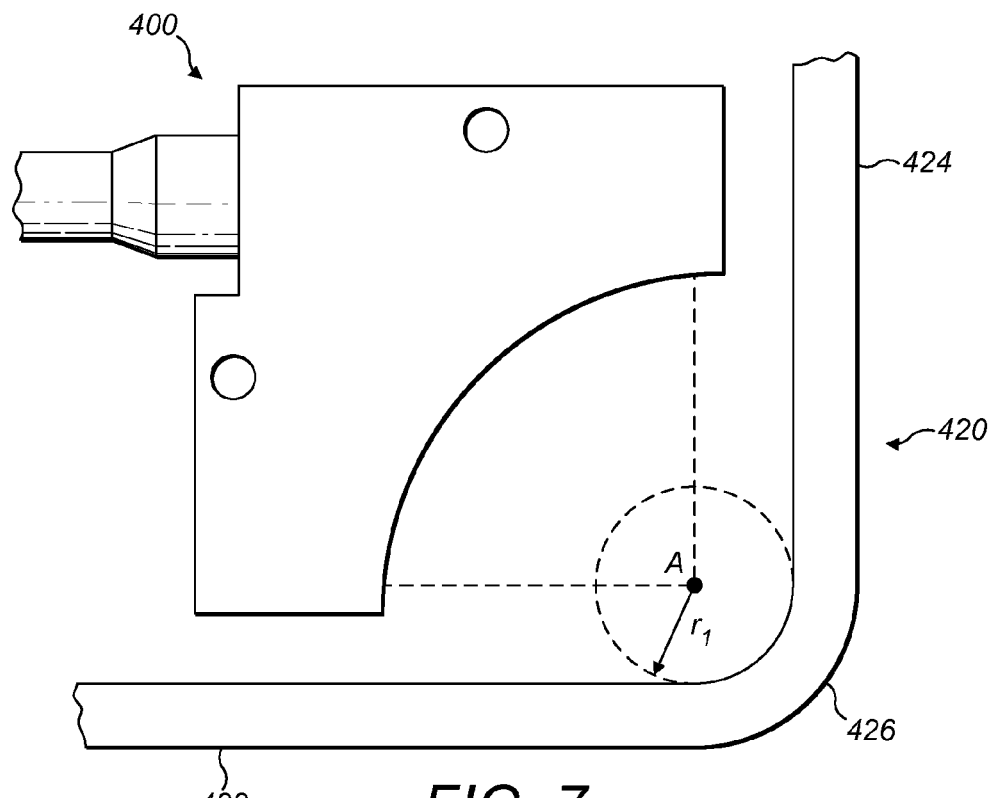
FIG. 7 is a schematic side view of a curved array being used to scan a concave radiussed workpiece.

Referring to FIG. 7, the curved array probe 400 is shown proximate a concave workpiece 420 having a first leg 422, a second leg 424 and a radiussed section 426 disposed therebetween. The radiussed section 426 has a radius R1 and describes an angle of 90 degrees such that the first and second leg 422 and 444 are substantially perpendicular.

The natural focal point of the array A is aligned with the centre point of the radius R1 of the radius section 426. This ensures that the propagating wave front enters the workpiece 420 parallel to the surface. This prevents distortion and ensures that incident ultrasonic energy is reflected back to the originating element.

Figure 8:
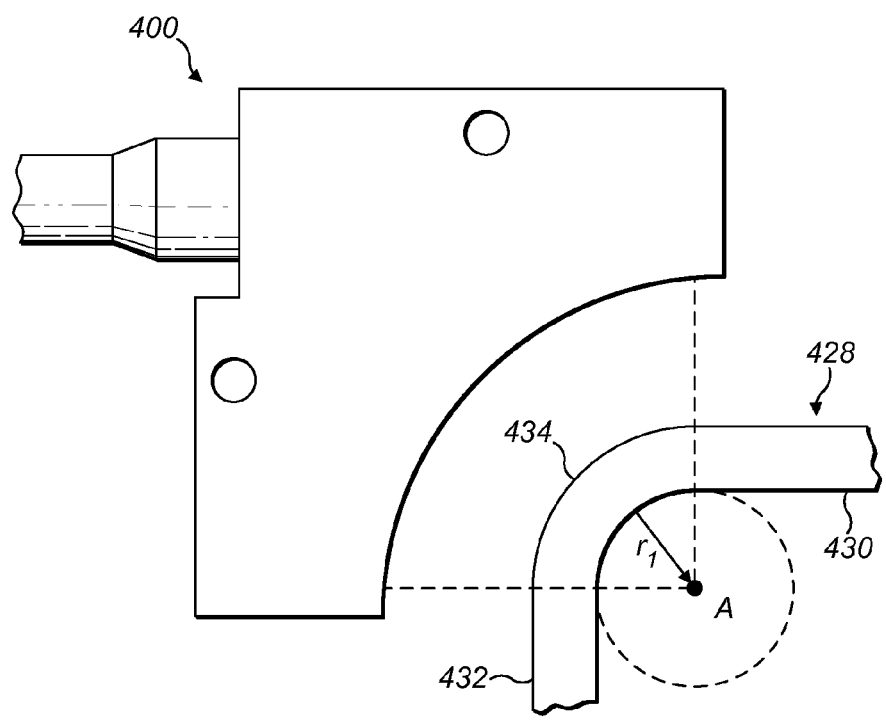
FIG. 8 is a side schematic view of a curved array being used to scan a convex radiussed workpiece.

Referring to FIG. 8, the same curved array probe 400 is used to scan a convex workpiece 428 having a first leg 430, a second leg 432 and a radiussed portion 434 defined therebetween.

Again it will be noted that the probe 400 is positioned such that the geometric focal point A is coincident with the centre of the radius of the radiussed portion 434.

In both situations, although positioning of the array in this manner provides for optimum coverage of the radiussed portion, and low distortion because the centre points are coincident, the focal point A is always outside of the thickness of the workpiece 420, 428. This means that the accuracy of the scan is not optimal and, as such, small discontinuities would not be detected.

Referring to FIGS. 9a to 11b, a method of improving the accuracy of the curved array probe of FIGS. 6 to 8 is shown.

Figure 9A:
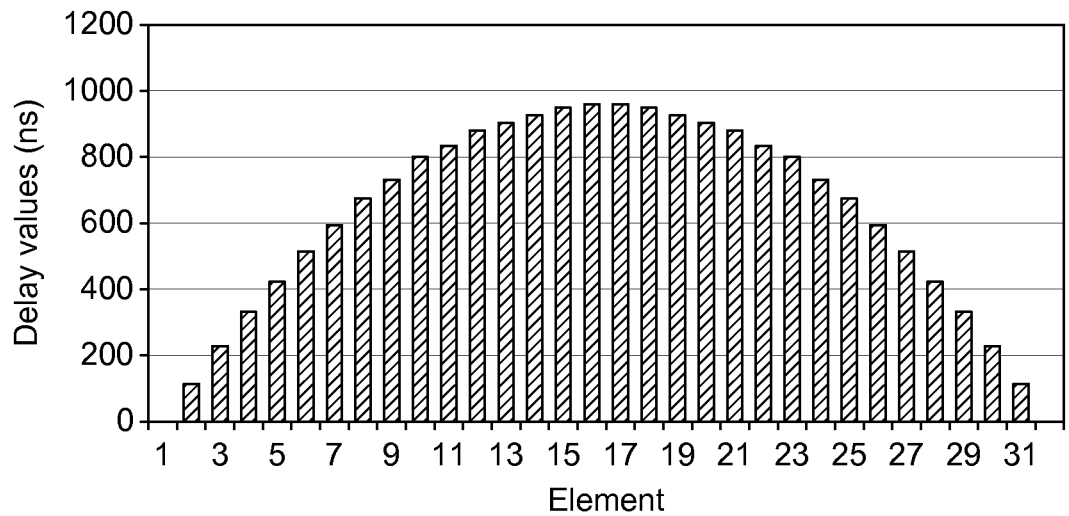
FIG. 9a is graph showing a first focal law.
Figure 9B:
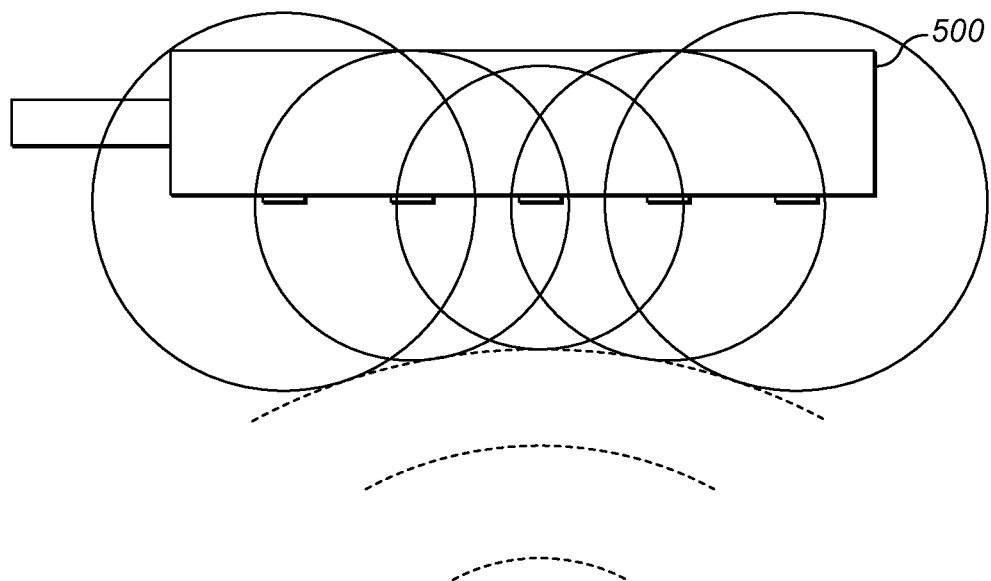
FIG. 9b is a schematic plan view of a linear array controlled by the first focal law.

FIG. 9a shows a focal law which, when applied to flat linear array 500 shown in FIG. 9b, provides a phased array focal point FP in a desired location.

Figure 10A:
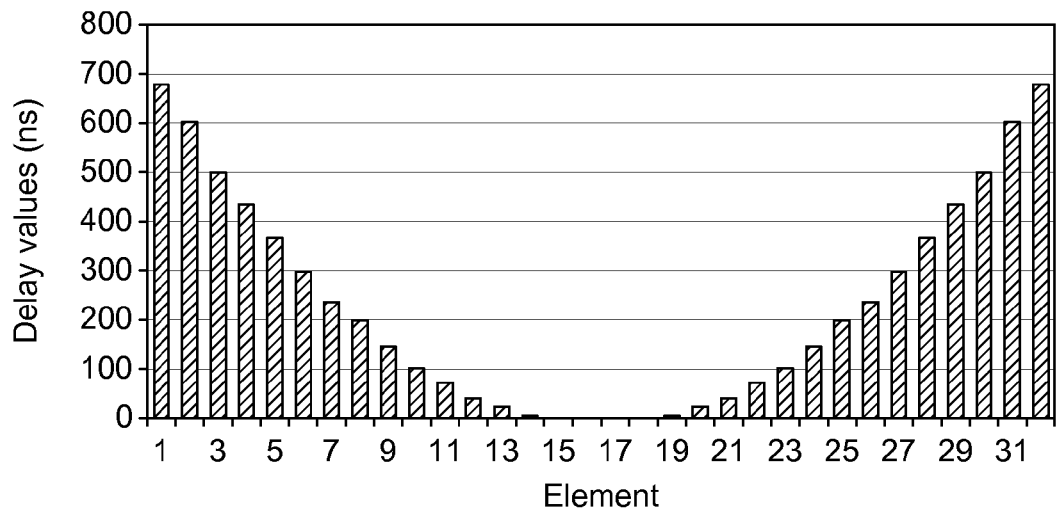
FIG. 10a is a graph of a second focal law.
Figure 10B:
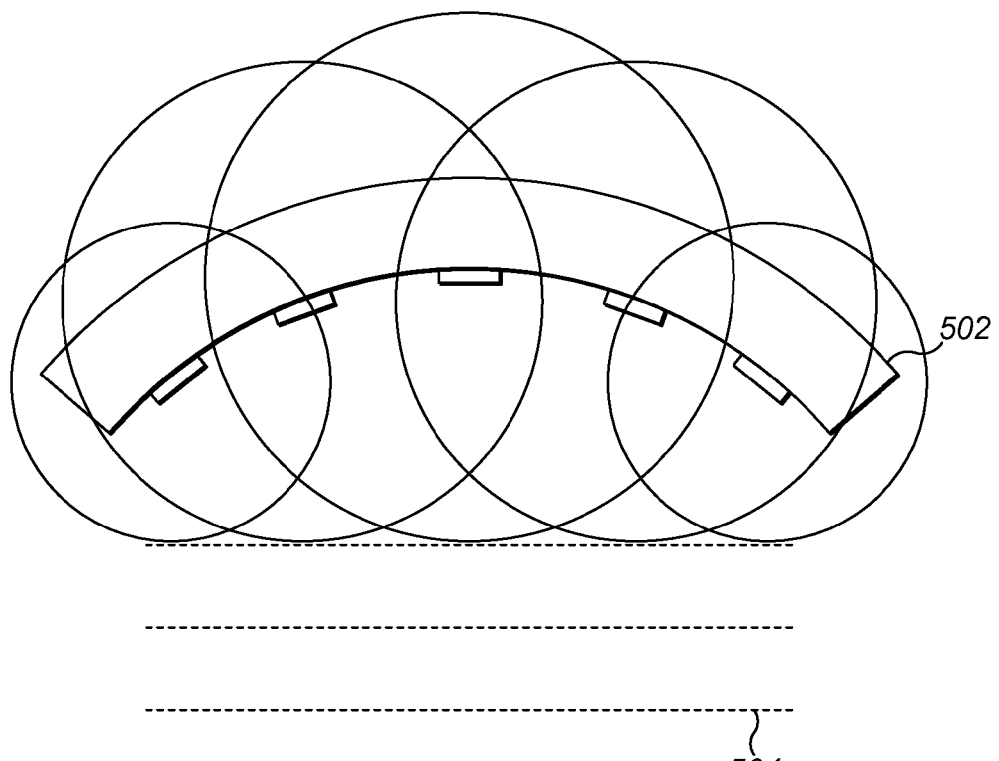
FIG. 10b is a schematic plan view of a curved array controlled by the second focal law.

FIG. 10a shows a focal law which when applied to a circular curved array as shown in FIG. 10b, defocuses the array so as to provide a progressive linear wave front 504. As such, referring to FIGS. 7 and 8, the invention provides a method of moving the focal point of the array 400a into the workpiece 420, 428. By firstly applying the focal law as shown in FIG. 10a, a linear wave front is produced. In other words, the curved array probe 400 acts as a linear probe. If the focal law shown in FIG. 9a is then applied, the focal point FP can be moved into the thickness of the material thus providing the required resolution.

Figure 11A:
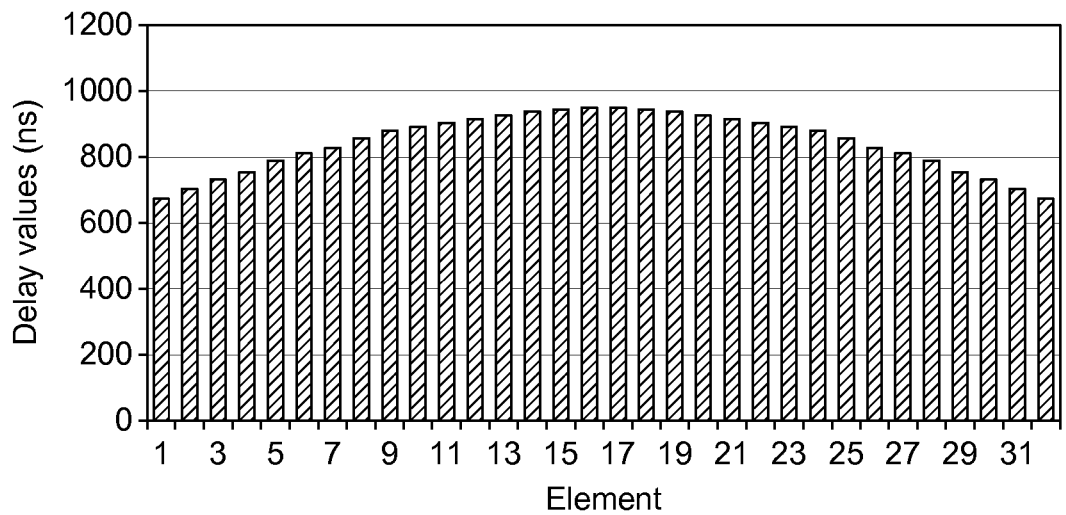
FIG. 11a is a graph of a combined focal law.
Figure 11B:
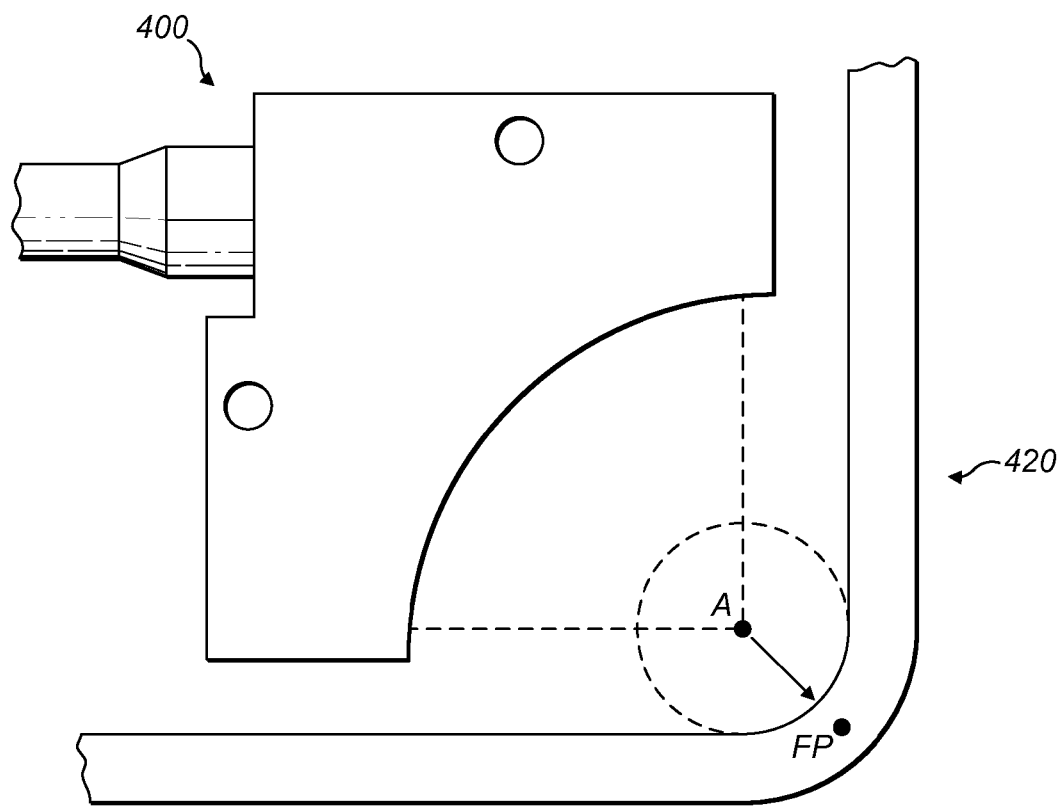
FIG. 11b is a schematic plan view of a curved array scanning a convex radius workpiece being controlled by the combined focal law.

As such, the combined focal law produced by the summation of those shown in FIG. 9a and FIG. 10a allows the focal point to be moved to the desired location within the material. Referring to FIG. 11a, a resulting focal law which is summation of those shown in FIGS. 9a and 10a is shown. When applied to the curved array probe 400, shown in FIG. 11b, the geometric focal point A moves into the material to focal point FP. As such, the curved array probe 400 is able to better image small discontinuities in the material of the workpiece 420.

This technique focusses the energy in the first (XY) plane—i.e. the plane of the array curvature. Focussing in a series of second planes perpendicular to XY, and therefore the page with respect to FIG. 11a (and therefore parallel to Z) can be achieved by using a focussing shoe 308.

It will be appreciated that the above method can be used on any type of curved array probe and with flexible arrays. In particular, the above technique can be used with arrays with shaped or curved elements to provide additional focussing.

The invention claimed is:

1. A method of scanning a curved engineering component comprising the steps of:
   providing a probe having a curved ultrasonic array having a plurality of elements arranged in a curved path having a geometric focal point,
   providing a control system configured to fire the elements of the array according to a predetermined focal law,
   providing a curved engineering component having a radius and centre of curvature, which centre of curvature is outside the component,
   aligning the geometric focal point of the array and the centre of curvature of the curved engineering component,
   using the control system to activate the elements of the array according to a focal law to move a focal point of the array away from the geometric focal point into the curved engineering component.

2. The method according to claim 1 in which the curved path of the curved ultrasonic array defines a first plane, the method comprising the step of:
   providing a focussing element for the curved ultrasonic array comprising a curved surface arranged to focus ultrasonic energy from the array,
   positioning the scanning element proximate the array to focus ultrasonic energy from the array in a second plane, perpendicular to the first plane.

3. The method according to claim 2 in which the focussing element comprises:
   a first, input, surface proximate the array, the first surface being flat in the second plane, and;
   a second, output, surface being curved in the second plane to focus ultrasonic energy leaving the focussing element.

4. The method of scanning an engineering component according to claim 1, in which the curved path is a circle segment having a geometric focal point at the origin of the circle segment.

5. The method of scanning an engineering component according to claim 1, in which the workpiece comprises a radiused portion.

6. The method of scanning an engineering component according to claim 1 in which the ultrasonic array is flexible.

7. An engineering component inspection ultrasonic probe for inspection of a radiused component having a centre of curvature, the centre is outside the radiused component, comprising:

a probe having a curved ultrasonic array having a plurality of elements arranged in a curved path having a geometric focal point, the geometric focal point of the array being configured to align with the centre of curvature of the radiused component, a control system configured to fire the elements of the array according to a predetermined focal law, which the control system is configured to activate the elements of the array according to a focal law to move a focal point of the array away from the geometric focal point into the radiused component.

8. The engineering component inspection ultrasonic probe according to claim 7, in which the curved path lies in a first plane, and in which the probe comprises:

a focussing element comprising a curved surface arranged to focus ultrasonic energy from the array in a second plane, perpendicular to the first plane.

9. The engineering component inspection ultrasonic probe according to claim 8, in which the curved surface is concave.

10. The engineering component inspection ultrasonic probe according to claim 9, in which the curved surface describes a concave circle segment in cross section.

11. The engineering component inspection ultrasonic probe according to claim 8, in which the focussing element comprises an input surface proximate the array, which input surface is flat in the second plane.

12. The engineering component inspection ultrasonic probe according to claim 8, in which the focussing element comprises an input surface proximate the array, which input surface is curved in the first plane.

13. The engineering component inspection ultrasonic probe according to claim 8 in which the focussing element is replaceable.

14. The engineering component inspection ultrasonic probe according to claim 7 in which the ultrasonic array is flexible.

15. An apparatus comprising a radiused component having a centre of curvature, which centre of curvature is outside the component and an engineering component inspection ultrasonic probe for inspection of a radiused component having a centre of curvature, which centre is outside the radius component, comprising:

a probe having a curved ultrasonic array having a plurality of elements arranged in a curved path having a geometric focal point, the geometric focal point of the array being configured to align with the centre of curvature of the radiused component, a control system configured to fire the elements of the array according to a predetermined focal law, which the control system is configured to activate the elements of the array according to a focal law to move a focal point of the array away from the geometric focal point into the radiused components, wherein the geometric focal point of the array is aligned with the centre of curvature of the radiused component.

* * * * *